United States Patent
Sakai

(10) Patent No.: US 9,664,629 B2
(45) Date of Patent: May 30, 2017

(54) INDUSTRIAL MACHINE AND METHOD FOR MEASURING AMOUNT OF EXPANSION/CONTRACTION OF INDUSTRIAL MACHINE

(71) Applicant: MITUTOYO CORPORATION, Kanagawa (JP)

(72) Inventor: Hisayoshi Sakai, Kanagawa (JP)

(73) Assignee: MITUTOYO CORPORATION, Kanagawa (JP)

(*) Notice: Subject to any disclaimer, the term of this patent is extended or adjusted under 35 U.S.C. 154(b) by 381 days.

(21) Appl. No.: 14/514,882

(22) Filed: Oct. 15, 2014

(65) Prior Publication Data
US 2015/0131697 A1    May 14, 2015

(30) Foreign Application Priority Data
Nov. 11, 2013  (JP) .................................. 2013-232675

(51) Int. Cl.
| | |
|---|---|
| G01N 25/16 | (2006.01) |
| G01B 21/04 | (2006.01) |
| G01B 5/00 | (2006.01) |
| G01B 5/008 | (2006.01) |

(52) U.S. Cl.
CPC ............. *G01N 25/16* (2013.01); *G01B 5/008* (2013.01); *G01B 5/0014* (2013.01); *G01B 21/045* (2013.01)

(58) Field of Classification Search
USPC .............................. 374/55, 56, 141, 45, 100
See application file for complete search history.

(56) References Cited

U.S. PATENT DOCUMENTS

| | | | | |
|---|---|---|---|---|
| 4,923,307 A | * | 5/1990 | Gilmore ................. | G01N 25/16 336/136 |
| 5,009,512 A | * | 4/1991 | Lessi ....................... | G01B 7/16 33/557 |
| 6,532,680 B2 | * | 3/2003 | Braasch .................. | G01B 7/16 33/503 |
| 6,829,838 B1 | * | 12/2004 | Weekers .............. | G01B 5/0014 33/503 |
| 8,676,527 B2 | | 3/2014 | Ono et al. | |
| 2008/0033690 A1 | * | 2/2008 | Grupp .................. | G01B 21/042 702/152 |
| 2009/0195263 A1 | * | 8/2009 | Yano ................... | G01R 31/2891 324/762.06 |

(Continued)

FOREIGN PATENT DOCUMENTS

| | | |
|---|---|---|
| JP | 2001-021303 | 1/2001 |
| JP | 2012-53033 | 3/2012 |

*Primary Examiner* — Mirellys Jagan
(74) *Attorney, Agent, or Firm* — Greenblum & Bernstein, P.L.C.

(57) ABSTRACT

An industrial machine includes a moving mechanism moving one of a probe and a tool relative to a work piece, using three displacement axes parallel to each of three orthogonal axis directions; a low thermal expansion member formed with a material having a smaller thermal expansion coefficient than a material forming a structural element of the moving mechanism; and an expansion/contraction measurer measuring, using the low thermal expansion member as a reference, an amount of expansion/contraction of the structural element in one of the three orthogonal axis directions, the expansion/contraction occurring due to a change in temperature.

11 Claims, 13 Drawing Sheets

(56) References Cited

U.S. PATENT DOCUMENTS

| | | | | |
|---|---|---|---|---|
| 2010/0101104 A1* | 4/2010 | Grzesiak | ............ | G01B 21/042 33/502 |
| 2010/0299094 A1* | 11/2010 | Hsu | ............ | G01B 21/045 702/95 |
| 2012/0204435 A1* | 8/2012 | Nakajima | ............ | G01B 5/008 33/503 |
| 2012/0275486 A1* | 11/2012 | Bahr | ............ | G01N 25/16 374/55 |
| 2013/0047452 A1* | 2/2013 | McMurtry | ............ | G01B 5/0016 33/503 |
| 2015/0211835 A1* | 7/2015 | Merlo | ............ | G01B 5/0014 702/95 |
| 2015/0276633 A1* | 10/2015 | Koyama | ............ | G01M 99/002 702/94 |

* cited by examiner

INDUSTRIAL MACHINE AND METHOD FOR MEASURING AMOUNT OF EXPANSION/CONTRACTION OF INDUSTRIAL MACHINE

CROSS-REFERENCE TO RELATED APPLICATIONS

The present application claims priority under 35 U.S.C. §119 of Japanese Application No. 2013-232675, filed on Nov. 11, 2013, the disclosure of which is expressly incorporated by reference herein in its entirety.

BACKGROUND OF THE INVENTION

1. Field of the Invention

The present invention relates to an industrial machine used in measuring or processing a work piece, and to a method for measuring an amount of expansion/contraction of the industrial machine.

2. Description of Related Art

A coordinate measuring machine (industrial machine) used in measuring a work piece includes guidance corresponding to each of three mutually orthogonal axes; a movable body displacing along the guidance; a scale for measuring an amount of displacement of the movable body; and a probe detecting contact with the work piece (measured object). Such a coordinate measuring machine can obtain three-dimensional coordinate values of the probe from the amount of displacement in each of the axis directions. There is a great deal of variety in structural forms of coordinate measuring machines; however, a bridge displacement-type coordinate measuring machine is the most common.

The bridge displacement-type coordinate measuring machine has a structure in which drive guide mechanisms corresponding to each of the three mutually orthogonal axes are serially stacked. Specifically, the bridge displacement-type coordinate measuring machine includes a base, a Y-carriage, an X-slider, and a Z-ram. A Y-rail is fixated to the base, the Y-rail extending in a Y-axis direction. The Y-carriage is formed to have a bridge structure capable of being guided on the Y-rail and displaced over a top surface of the base. The Y-carriage includes a column, a supporter, and an X-beam supported by the column and supporter and extending in an X-axis direction. The X-slider is capable of being guided and displaced along the X-beam. The Z-ram is capable of being guided on a guide provided to the X-slider and displacing in a Z-axis direction. The Z-ram also holds the probe.

The bridge displacement-type coordinate measuring machine measures a position of the probe in each axis direction using an X-scale, a Y-scale, and a Z-scale. For example, the Z-axis direction position is measured by reading a value of the Z-scale, which is fixated to the Z-ram, with a Z-detection device provided to the X-slider. Moreover, a three-dimensional coordinate system configured by the X-scale, the Y-scale, and the Z-scale and provided to the coordinate measuring machine is referred to as a "machine coordinate system."

In this regard, in Japanese Patent Laid-open Publication No. 2001-021303, a temperature sensor is mounted to each of an X-scale, a Y-scale, and a Z-scale of a bridge displacement-type coordinate measuring machine. Even in a case where the scales expand and contract according to a thermal expansion coefficient inherent to the scale material due to changes in environmental temperature, an amount of expansion/contraction of the scales is corrected by temperature correction. However, when the column or supporter (structural components other than the scales) expands and contracts in the Z-axis direction due to a change in temperature, the Z-detection device provided to the X-slider is displaced in the Z-axis direction because the X-beam guiding the X-slider is supported by the column and the supporter. As a result, an error in the Z-axis direction may arise in the coordinate values of the probe.

Japanese Patent Laid-open Publication No. 2012-053033 discloses an invention conceived with a focus on the noted concern regarding Japanese Patent Laid-open Publication No. 2001-021303. Specifically, in Japanese Patent Laid-open Publication No. 2012-053033, in order to respond to the Z-axis direction displacement of the Z-detection device caused by the expansion/contraction of the column and the supporter due to a change in temperature, a temperature detection sensor is provided to the column and to the supporter to measure the temperature. Also, an estimated value for the amount of Z-axis direction expansion/contraction of the column and the supporter is calculated based on the temperature and the thermal expansion coefficient of the column and the supporter, and corrections are made based on the estimated value.

However, in carrying out the correction method disclosed in Japanese Patent Laid-open Publication No. 2012-053033, the estimated value for the amount of expansion/contraction calculated using the temperature and the thermal expansion coefficient of the column and the supporter does not necessarily reflect reality, and so the estimated value for the amount of expansion/contraction is unreliable.

In other words, the column and supporter of the coordinate measuring machine are large in size and mass, and so also have a large time constant for changes in temperature. Therefore, due to temperature distribution of the column and the supporter, the estimated value for the amount of expansion/contraction is unreliable. For example, in a case where the temperature detection sensor is positioned at a specific portion on a surface of each of the column and the supporter, there is unreliability due to a difference between a surface temperature and an internal temperature of the column and the supporter. In addition, unreliability of an official thermal expansion coefficient of a material forming the column and the supporter and unreliability of the temperature detection sensor both cause unreliability in the estimated value for the amount of expansion/contraction.

SUMMARY OF THE INVENTION

In order to resolve the above concerns, the present disclosure provides an industrial machine and a method for measuring an amount of expansion/contraction of the industrial machine capable of accurately measuring the amount of expansion/contraction due to a change in temperature.

An industrial machine according to an aspect of the present disclosure includes a moving mechanism moving one of a probe and a tool relative to a work piece, using three displacement axes parallel to each of three orthogonal axis directions; a low thermal expansion member formed with a material having a smaller thermal expansion coefficient than a material forming a structural element of the moving mechanism; and an expansion/contraction measurer measuring, using the low thermal expansion member as a reference, an amount of expansion/contraction of the structural element in one of the three orthogonal axis directions, the expansion/contraction occurring due to a change in temperature.

The three orthogonal axis directions may include an X-axis direction, a Y-axis direction, and a Z-axis direction.

The moving mechanism may include a base having a top surface on which the work piece is installed; a Y-carriage, which is a bridge structure supported by the base and moving in the Y-axis direction relative to the base; an X-slider supported by the Y-carriage and moving in the X-axis direction relative to the Y-carriage; and a Z-ram supported by the X-slider, moving in the Z-axis direction relative to the X-slider, and holding the probe or the tool. The top surface of the base is orthogonal to the Z-axis direction. The Y-carriage includes a column and a supporter, each standing upright along the Z-axis direction, separated from each other in the X-axis direction; and an X-beam supported by the column and the supporter and guiding the X-slider in the X-axis direction. In such a case, the low thermal expansion member preferably includes a first low thermal expansion member formed with a material having a smaller thermal expansion coefficient than the material forming the column; and a second low thermal expansion member formed with a material having a smaller thermal expansion coefficient than the material forming the supporter. The expansion/contraction measurer preferably measures the amount of Z-axis direction expansion/contraction of the column using the first low thermal expansion member as a reference, and measures the amount of Z-axis direction expansion/contraction of the supporter using the second low thermal expansion member as the reference.

The low thermal expansion member preferably further includes a third low thermal expansion member formed with a material having a smaller thermal expansion coefficient than the material forming the column. The first low thermal expansion member is preferably positioned at a first position of the column and the third low thermal expansion member is preferably positioned at a second position of the column separated from the first position in the Y-axis direction. The expansion/contraction measurer preferably measures the amount of Z-axis direction expansion/contraction of the column in the first position using the first low thermal expansion member as the reference, and measures the amount of Z-axis direction expansion/contraction of the column in the second position using the third low thermal expansion member as the reference.

The industrial machine preferably further includes a Z-scale fixated to the Z-ram and extending in the Z-axis direction; and a Z-detection device provided to the X-slider and reading a value of the Z-scale. In such a case, the first low thermal expansion member preferably includes a first top end and a first bottom end, provided in a hollow space formed on an interior of the column and positioned respectively at each of two Z-axis direction sides. The first bottom end is preferably fixated so as to prevent displacement in the Z-axis direction relative to a base-side end of the column. The first top end is preferably allowed to freely displace in the Z-axis direction relative to the column due to a difference in thermal expansion between the first low thermal expansion member and the column. The second low thermal expansion member preferably includes a second top end and a second bottom end, provided in a hollow space formed on an interior of the supporter and positioned respectively at each of two Z-axis direction sides. The second bottom end is preferably fixated so as to prevent displacement in the Z-axis direction relative to a base-side end of the supporter. The second top end is preferably allowed to freely move in the Z-axis direction relative to the supporter due to a difference in thermal expansion between the second low thermal expansion member and the supporter. The expansion/contraction measurer preferably measures the amount of Z-axis direction expansion/contraction of the column using the first top end as the reference, and measures the amount of Z-axis direction expansion/contraction of the supporter using the second top end as the reference. Z-axis direction positions of the first bottom end and the second bottom end preferably substantially match a Z-axis direction position of the top surface of the base. Z-axis direction positions of the first top end and the second top end preferably substantially match a Z-axis direction position of a detection reference point of the Z-detection device.

The three orthogonal axis directions may include the X-axis direction, the Y-axis direction, and the Z-axis direction. The moving mechanism may include a base; a Y-table supported by the base and moving in the Y-axis direction relative to the base; a fixed bridge fixated to the base; an X-slider supported by the fixed bridge and moving in the X-axis direction relative to the fixed bridge; and a Z-ram supported by the X-slider, moving in the Z-axis direction relative to the X-slider, and holding the probe or the tool. A top surface on which the work piece is installed is formed on the Y-table. The top surface of the table is orthogonal to the Z-axis direction. The fixed bridge includes a first column and a second column, each standing upright along the Z-axis direction on two sides in the X-axis direction straddling the Y-table; and an X-beam supported by the first column and the second column and guiding the X-slider in the X-axis direction. In such a case, the low thermal expansion member preferably includes a first low thermal expansion member formed with a material having a smaller thermal expansion coefficient than the material forming the first column; and a second low thermal expansion member formed with a material having a smaller thermal expansion coefficient than the material forming the second column. The expansion/contraction measurer preferably measures the amount of Z-axis direction expansion/contraction of the first column using the first low thermal expansion member as the reference, and measures the amount of Z-axis direction expansion/contraction of the second column using the second low thermal expansion member as the reference.

The industrial machine may further include a Z-scale fixated to the Z-ram and extending in the Z-axis direction; and a Z-detection device provided to the X-slider and reading a value of the Z-scale. In such a case, the first low thermal expansion member preferably includes a first top end and a first bottom end, provided in a hollow space formed on an interior of the first column and positioned respectively at each of two Z-axis direction sides. The first bottom end is preferably fixated so as to prevent displacement in the Z-axis direction relative to a base-side end of the first column. The first top end is preferably allowed to freely displace in the Z-axis direction relative to the first column due to a difference in thermal expansion between the first low thermal expansion member and the first column. The second low thermal expansion member preferably includes a second top end and a second bottom end, provided in a hollow space formed on an interior of the second column and positioned respectively at each of two Z-axis direction sides. The second bottom end is preferably fixated so as to prevent displacement in the Z-axis direction relative to a base-side end of the second column. The second top end is preferably allowed to freely move in the Z-axis direction relative to the second column due to a difference in thermal expansion between the second low thermal expansion member and the second column. The expansion/contraction measurer preferably measures the amount of Z-axis direction expansion/contraction of the first column using the first top end as a reference, and measures the amount of Z-axis direction expansion/contraction of the second column using the second top end as the reference. Z-axis direction positions of the first bottom end and the second bottom end preferably substantially match a Z-axis direction position of the top surface of the Y-table. Z-axis direction positions of the first top end and the second top end preferably substantially match a Z-axis direction position of a detection reference point of the Z-detection device.

The low thermal expansion member may also be provided outside the structural element in a case where, for example, no hollow space is formed on an interior of the structural element (e.g., the column, the supporter, the first column, the second column).

The expansion/contraction measurer preferably includes a differential transformer-type displacement sensor having a contact stylus head, an eddy current-type displacement sensor, a capacitance-type displacement sensor, or an optical displacement sensor.

The industrial machine preferably further includes a temperature detection sensor and an expansion/contraction corrector. The temperature detection sensor detects the temperature of the low thermal expansion member. The expansion/contraction corrector calculates the amount of expansion/contraction of the low thermal expansion member based on the temperature, the thermal expansion coefficient of the low thermal expansion member, and dimensions of the low thermal expansion member at a reference temperature, and corrects the amount of expansion/contraction of the structural element based on the amount of expansion/contraction of the low thermal expansion member.

A method for measuring an amount of expansion/contraction of an industrial machine according to another aspect of the present disclosure includes a moving mechanism moving one of a probe and a tool relative to a work piece, using three displacement axes parallel to each of three orthogonal axis directions. The method measures, using a low thermal expansion member as a reference, an amount of expansion/contraction of a structural element of the moving mechanism in one of the three orthogonal axis directions, the expansion/contraction occurring due to a change in temperature and the low thermal expansion member being formed with a material having a smaller thermal expansion coefficient than a material forming the structural element of the moving mechanism.

The present disclosure provides an industrial machine and a method for measuring an amount of expansion/contraction of the industrial machine capable of accurately measuring the amount of expansion/contraction due to a change in temperature.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

Figure 1:
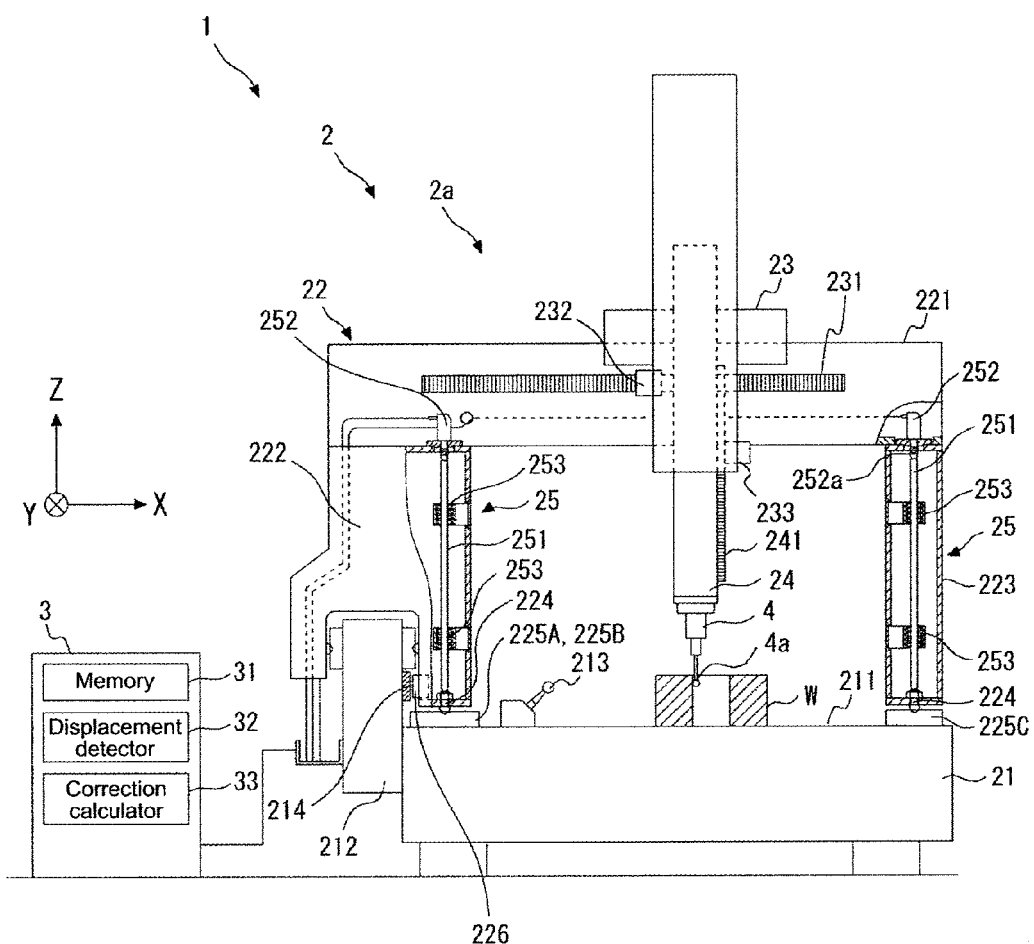
FIG. 1 illustrates a schematic configuration of a coordinate measuring machine (industrial machine) according to a first embodiment.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

First Embodiment

Hereafter, an embodiment of the present disclosure is described with reference to the drawings. Identical reference numerals are assigned to identical elements in each of the plurality of drawings, and duplicative descriptions are omitted where necessary.

FIG. 1 illustrates a schematic configuration of a coordinate measuring machine (an industrial machine) according to a first embodiment. In FIG. 1, a coordinate measuring machine 1 includes a measurer main body 2; a controller 3 executing drive control of the measurer main body 2, a process calculating three-dimensional coordinate values, and the like; and a probe 4 outputting to the controller 3 a signal indicating contact between a stylus head 4a and a work piece W (measured object) or a signal for an amount of displacement of the stylus head 4a due to the contact. The coordinate measuring machine 1 is a bridge displacement-type coordinate measuring machine. In addition, in some cases, the coordinate measuring machine 1 is referred to as a bridge structure-type machine having triaxial orthogonal coordinates.

The measurer main body 2 includes a moving mechanism 2a moving the probe 4 in three orthogonal axis directions, configured by an X-axis direction, a Y-axis direction, and a Z-axis direction. The moving mechanism 2a includes a base 21, a Y-rail 212, a Y-carriage 22, an X-slider 23, and a Z-ram 24 as primary structural components. The base 21 is installed in a predetermined position on an installation floor. The Y-rail 212 is fixated to the base 21 and extends in the Y-axis direction. The Y-carriage 22 is capable of movement along the Y-rail 212 over a top surface 211 of the base 21. The X-slider 23 is supported by the Y-carriage 22 and is capable of movement relative to the Y-carriage 22 in the X-axis direction. The Z-ram 24 is supported by the X-slider 23 and is capable of movement relative to the X-slider 23 in the Z-axis direction. The Z-ram 24 also holds the probe 4.

The work piece W and a master ball 213 are placed on the top surface 211 of the base 21. The top surface 211 is orthogonal to the Z-axis direction. The Y-carriage 22 is a bridge structure supported by the base 21, guided by the Y-rail 212, and moving relative to the base 21 in the Y-axis direction. The Y-carriage 22 includes a column 222 and a supporter 223, each standing upright along the Z-axis direction, and an X-beam 221 extending in the X-axis direction. The column 222 and the supporter 223 are separated from each other in the X-axis direction.

The X-beam 221 is supported by the column 222 and the supporter 223, and guides the X-slider 23. The X-slider 23 is capable of displacement along the X-beam 221. The Z-ram 24 is capable of movement in the Z-axis direction along a guide provided to an interior of the X-slider 23. Specifically, the moving mechanism 2a can move the probe 4 (the Z-ram 24 holding the probe 4) relative to the work piece W (the base 21 on which the work piece W is placed) using three movement axes parallel to the X-, Y-, and Z-axis directions, respectively.

A Z-axis direction (perpendicular direction) weight of the Y-carriage 22 is supported at three locations in total: air pads 225A and 225B provided to a bottom end surface of the column 222, and an air pad 225C provided to a bottom end surface of the supporter 223. The air pads 225A and 225B are separated from each other in the Y-axis direction. Each of the air pads 225A to 225C are static pressure gas bearings. In addition, an adjustment screw 224 is provided to each of a joint between the column 222 and the air pad 225A, a joint between the column 222 and the air pad 225B, and a joint between the supporter 223 and the air pad 225C. A support height at the three points can be adjusted such that movement of the X-slider 23 is parallel to the top surface 211.

Figure 2:
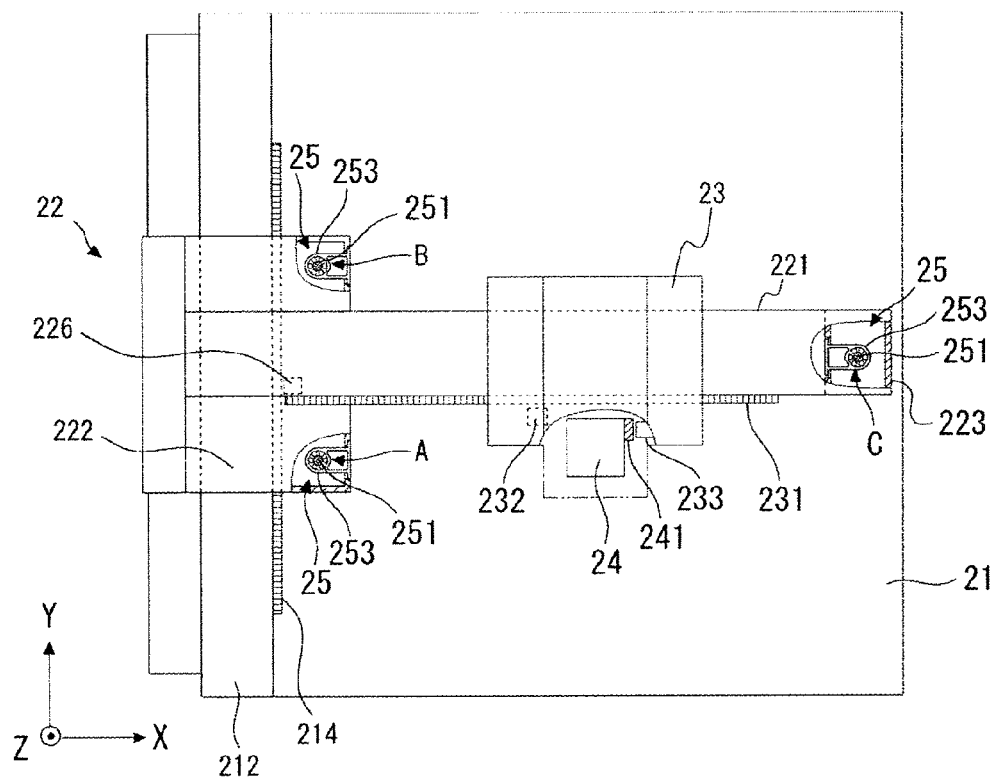
FIG. 2 is a plan view of a measurer main body of the coordinate measuring machine according to the first embodiment.

FIG. 2 illustrates the measurer main body 2 as viewed from above on the Z-axis. Z correction reference units 25 are provided to positions A to C, which correspond to the air pads 225A to 225C, respectively. The Z correction reference units 25 are provided above each of the air pads 225A to 225C. The Z correction reference unit 25 includes a low thermal expansion shaft 251 (low thermal expansion member) and a guide unit 253. The Z correction reference unit 25 is described in further detail below.

Returning to FIG. 1, a hollow space is formed on an interior of the column 222 and the supporter 223. The Z correction reference unit 25 provided at position A (corresponding to the air pad 225A) includes the low thermal expansion shaft 251, which is provided on an axis of the adjustment screw 224 corresponding to the air pad 225A; the guide unit 253 supporting the low thermal expansion shaft 251 within the hollow space of the column 222 so as to be parallel to the Z-axis direction; and a displacement sensor 252 detecting a relative Z-axis direction displacement of the column 222 at the position A, using the low thermal expansion shaft 251 as a reference.

The Z correction reference unit 25 provided at position B (corresponding to the air pad 225B) includes the low thermal expansion shaft 251, which is provided on the axis of the adjustment screw 224 corresponding to the air pad 225B; the guide unit 253 supporting the low thermal expansion shaft 251 within the hollow space of the column 222 so as to be parallel to the Z-axis direction; and the displacement sensor 252 detecting the relative Z-axis direction displacement of the column 222 at the position B, using the low thermal expansion shaft 251 as a reference.

The Z correction reference unit 25 provided at position C (corresponding to the air pad 225C) includes the low thermal expansion shaft 251, which is provided on the axis of the adjustment screw 224 corresponding to the air pad 225C; the guide unit 253 supporting the low thermal expansion shaft 251 within the hollow space of the supporter 223 so as to be parallel to the Z-axis direction; and the displacement sensor 252 detecting the relative Z-axis direction displacement of the supporter 223 at the position C, using the low thermal expansion shaft 251 as a reference.

The low thermal expansion shaft 251 is formed by a low thermal expansion material which is robust against changes in temperature. Accordingly, a thermal expansion coefficient of the material forming the low thermal expansion shaft 251 installed at positions A and B is smaller than the thermal expansion coefficient of the material forming the column 222, and the thermal expansion coefficient of the material forming the low thermal expansion shaft 251 installed at position C is smaller than the thermal expansion coefficient of the material forming the supporter 223.

A bottom end of the low thermal expansion shaft 251 is positioned proximate to the top surface 211 and is in contact with a head portion of the adjustment screw 224. Accordingly, the bottom end of the low thermal expansion shaft 251 is a fixed end fixated so as to prevent displacement in the Z-axis direction relative to a bottom end (base 21-side end) of the column 222 or the supporter 223. Moreover, positioning the low thermal expansion shaft 251 on a center axis of the air pads 225A to 225C (on the axis of the adjustment screw 224) is not strictly required.

By providing a stroke bearing, for example, the guide unit 253 supports the low thermal expansion shaft 251 without restricting relative Z-axis direction displacement due to a difference in an amount of expansion/contraction between the low thermal expansion shaft 251 and the column 222 or the supporter 223. Accordingly, a top end of the low thermal expansion shaft 251 is a free end allowing unrestricted displacement in the Z-axis direction relative to a top end of the column 222 or the supporter 223 due to a difference in thermal expansion between the low thermal expansion shaft 251 and the column 222 or the supporter 223.

The displacement sensor 252 is positioned on the top end (e.g., a top surface) of the column 222 or the supporter 223. The top end of the column 222 or the supporter 223 is an X-beam 221-side end. The displacement sensor 252 includes a plunger-type contact stylus head 252a, which moves in the Z-axis direction. A tip of the contact stylus head 252a makes contact with the top end (e.g., the top surface) of the low thermal expansion shaft 251. The displacement sensor 252 is, for example, a differential transformer-type displacement sensor. The displacement sensor 252 at position A directly measures, using the top end of the low thermal expansion shaft 251 provided to position A as the reference, an amount of Z-axis direction expansion/contraction of the column 222 at position A, the expansion/contraction occurring due to a change in temperature, then outputs a measurement signal to the controller 3. The displacement sensor 252 at position B directly measures, using the top end of the low thermal expansion shaft 251 provided to position B as the reference, the amount of Z-axis direction expansion/contraction of the column 222 at position B, the expansion/contraction occurring due to a change in temperature, then outputs the measurement signal to the controller 3. The displacement sensor 252 at position C directly measures, using the top end of the low thermal expansion shaft 251 provided to position C as the reference, the amount of Z-axis direction expansion/contraction of the supporter 223 at position C, the expansion/contraction occurring due to a change in temperature, then outputs the measurement signal to the controller 3.

Accordingly, the amount of expansion/contraction due to a change in temperature can be accurately measured for the column 222 and the supporter 223, which are structural elements of the moving mechanism 2a of the coordinate measuring machine 1. In addition, a method for measuring the amount of expansion/contraction according to the present embodiment is simple in comparison to a method providing a plurality of temperature detection sensors on the column 222 and the supporter 223 to measure the temperature and estimating the amount of expansion/contraction based on the temperature and thermal expansion coefficient of the column 222 and the supporter 223.

The measurer main body 2 includes an X-scale 231 and an X-detection device 232 for measuring an amount of X-axis direction displacement of the probe 4; a Y-scale 214 and a Y-detection device 226 for measuring an amount of Y-axis direction displacement of the probe 4; and a Z-scale 241 and a Z-detection device 233 for measuring an amount of Z-axis direction displacement of the probe 4. The X-scale 231 is fixated to the X-beam 221 and extends in the X-axis direction. The X-detection device 232 is provided to the X-slider 23 and reads a value of the X-scale 231, then outputs to the controller 3 a signal indicating a read result. The Y-scale 214 is fixated to the Y-rail 212 and extends in the Y-axis direction. The Y-detection device 226 is provided to the column 222 and reads a value of the Y-scale 231, then outputs to the controller 3 a signal indicating the read result. The Z-scale 241 is fixated to the Z-ram 24 and extends in the Z-axis direction. The Z-detection device 233 is provided to the X-slider 23 and reads a value of the Z-scale 241, then outputs to the controller 3 a signal indicating the read result.

The controller 3 is configured to include a CPU (Central Processing Unit), a memory, and the like, and further includes a memory 31, a displacement detector 32, and a correction calculator 33. The memory 31 stores information used by the controller 3. The functions of the displacement detector 32 and the correction calculator 33 are described hereafter.

Figure 3:
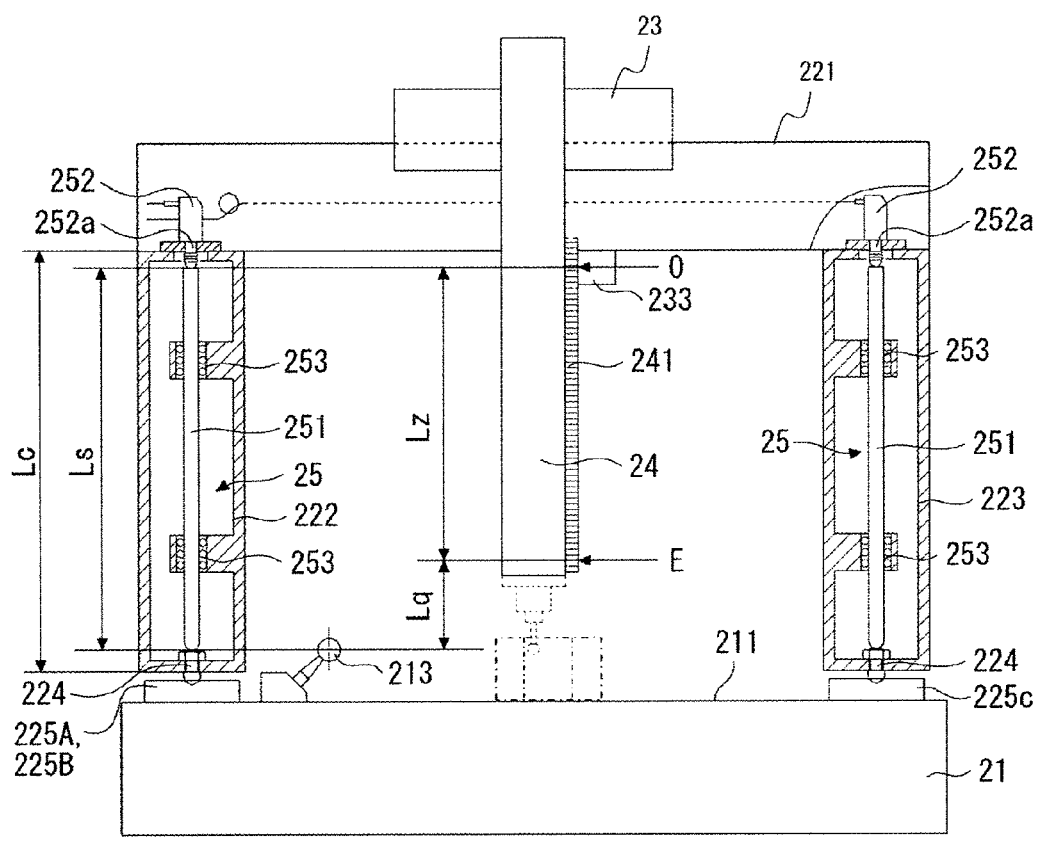
FIG. 3 illustrates extraction of an element related to Z-axis direction displacement of the coordinate measuring machine according to the first embodiment.

In order to illustrate correcting displacement of a Z-axis coordinate due to a change in temperature, FIG. 3 shows extracted elements related to a Z-axis direction change in position in the coordinate measuring machine 1. A height of the column 222 is defined as Lc, while a length of the low thermal expansion shaft 251 is defined as Ls. A fixed point E on the Z-scale 241 is fixed at a forefront end (probe 4-side end) of the Z-ram 24. Portions of the Z-scale 241 other than the fixed point E are mounted to the Z-ram 24 such that a difference in expansion/contraction between the Z-scale 241 and the Z-ram 24 due to a change in temperature can be ignored. The fixed point E may also be referred to as the bottom end of a Z-scale graduation detection. In a case where the thermal expansion coefficient of the Z-scale 241 is smaller than the thermal expansion coefficient of the Z-ram 24, the fixed point E is preferably close to the probe 4. A distance (O-E) between the fixed point E and a detection reference point O of the Z-detection device 233 when the Z-ram 24 has been lowered to the bottom-most end is defined as a Z-axis measurement range Lz. A Z-axis direction position of the Z-detection device 233 detection reference point O matches a Z-axis direction position of the top end of the low thermal expansion shaft 251. The detection reference point O may also be referred to as a scale detection reference point.

The displacement detector 32 calculates an amount of displacement based on the measurement signal output by the displacement sensor 252. For example, the displacement detector 32 calculates the amount of Z-axis direction displacement of the X-slider 23 or the Z-ram 24 caused by expansion and contraction of the column 222 and the supporter 223. The correction calculator 33 performs correction based on the amount of displacement calculated by the displacement detector 32. In other words, the controller 3 can calculate coordinates of the probe 4 or the work piece W based on the amount of Z-axis direction expansion/contraction of the column 222 and the supporter 223 due to a change in temperature.

Typically, the work piece W and the master ball 213 are placed on the top surface 211 of the base 21. A spherical center coordinate of the master ball 213 is a reference point for coordinates on the work piece W side, called a "work piece coordinate system." Accordingly, when rephrasing the technical issues involved in Japanese Patent Laid-open Publication Nos. 2001-021303 and 2012-053033, a "machine coordinate system" (configured by the X-scale 231, the Y-scale 214, and the Z-scale 241) and the "work piece coordinate system" undergo relative displacement in the Z-axis direction due to a change in temperature.

Given the above, the Z-axis direction displacement due to a change in temperature can be corrected using the amount of Z-axis direction expansion/contraction of the column 222 and the supporter 223, which is measured by the Z correction reference unit 25. Accordingly, the Z coordinate in the "machine coordinate system" of the coordinate measuring machine 1 can achieve a degree of thermal stability equivalent to a case where the column 222 and the supporter 223 are formed with a low thermal expansion material. Moreover, although the amount of expansion/contraction of the probe length Lp due to a change in temperature cannot be corrected by the Z correction reference unit 25, expansion and contraction of the probe length Lp due to a change in temperature is typically not a concern due to the probe length Lp being comparatively short and, in addition, due to techniques such as forming a casing of the probe 4 with low thermal expansion material. The amount of expansion/contraction of the probe length Lp may also be corrected based on a temperature and a thermal expansion coefficient of the probe 4 and a portion of the Z-ram 24 lower than the fixed point E.

Furthermore, because the amounts of Z-axis direction expansion/contraction of the column 222 and the supporter 223 are measured individually, sloping of the X-beam 221 in the XZ plane and slant of the Z axis in the XZ plane (rotation of the Z axis around the Y axis) can be detected. Moreover, the amounts of Z-axis direction expansion/contraction of the column 222 at positions A and B, which are separated from each other in the Y-axis direction, are measured individually.

Therefore, slant of the Z axis in the YZ plane (rotation of the Z axis around the X axis) can be detected.

In addition, the Z-axis direction position of the bottom end of the low thermal expansion shaft 251 (the fixed end) substantially matches the Z-axis direction position of the top surface 211 of the base 21, where the work piece W and the master ball 213 are installed. The Z-axis direction position of the top end of the low thermal expansion shaft 251 (the reference point for measuring the amount of expansion/contraction) substantially matches the Z-axis direction position of the detection reference point O of the Z-detection device 233. Therefore, the relative Z-axis direction displacement in the "machine coordinate system" and the "work piece coordinate system" due to a change in temperature can be more accurately detected. Moreover, when the Z-scale 241 is positioned higher in order to prevent the Z-scale 241 and the work piece W from interfering with and damaging each other due to mishandling during measurement, the Z-detection device 233 must also be positioned higher. In such a case, the top end of the low thermal expansion shaft 251 is positioned within the hollow space formed on the interior of the X-beam 221, and the displacement sensor 252 is fixated to the X-beam 221.

Furthermore, the low thermal expansion shaft 251 is positioned in the hollow space formed on the interior of the column 222 and the supporter 223. Therefore, the low thermal expansion shaft 251 is unlikely to be influenced by environmental changes in temperature.

Super Invar (FN-315) or Invar (FN-36) are appropriate low thermal expansion materials to form the low thermal expansion shaft 251. However, fused quartz or a low thermal expansion glass ceramic can also be used. By using a low thermal expansion shaft 251 formed with Super Invar or Invar, cost can be reduced as compared to a case where the column 222 or the supporter 223 are formed with Super Invar or Invar. Moreover, the weight of the X-beam 221, for example, is not applied to the low thermal expansion shaft 251, unlike the column 222 and the supporter 223, and therefore the low thermal expansion shaft 251 can be formed using a highly fragile material. In addition, as long as the low thermal expansion shaft 251 is rod-shaped, the cross-section shape is not limited to circular.

Above, the coordinate measuring machine 1 was described as an exemplary industrial machine according to the first embodiment. The industrial machine according to the first embodiment may also be a machine tool. In such a case, the Z-ram 24 holds the probe 4 or a tool for processing the work piece W.

Second Embodiment

Next, an industrial machine according to a second embodiment is described. Descriptions of aspects common to both the first and second embodiments may be omitted. Hereafter, a case is described where the industrial machine according to the second embodiment is a coordinate measuring machine; however, the industrial machine according to the second embodiment may also be a machine tool.

Figure 4:
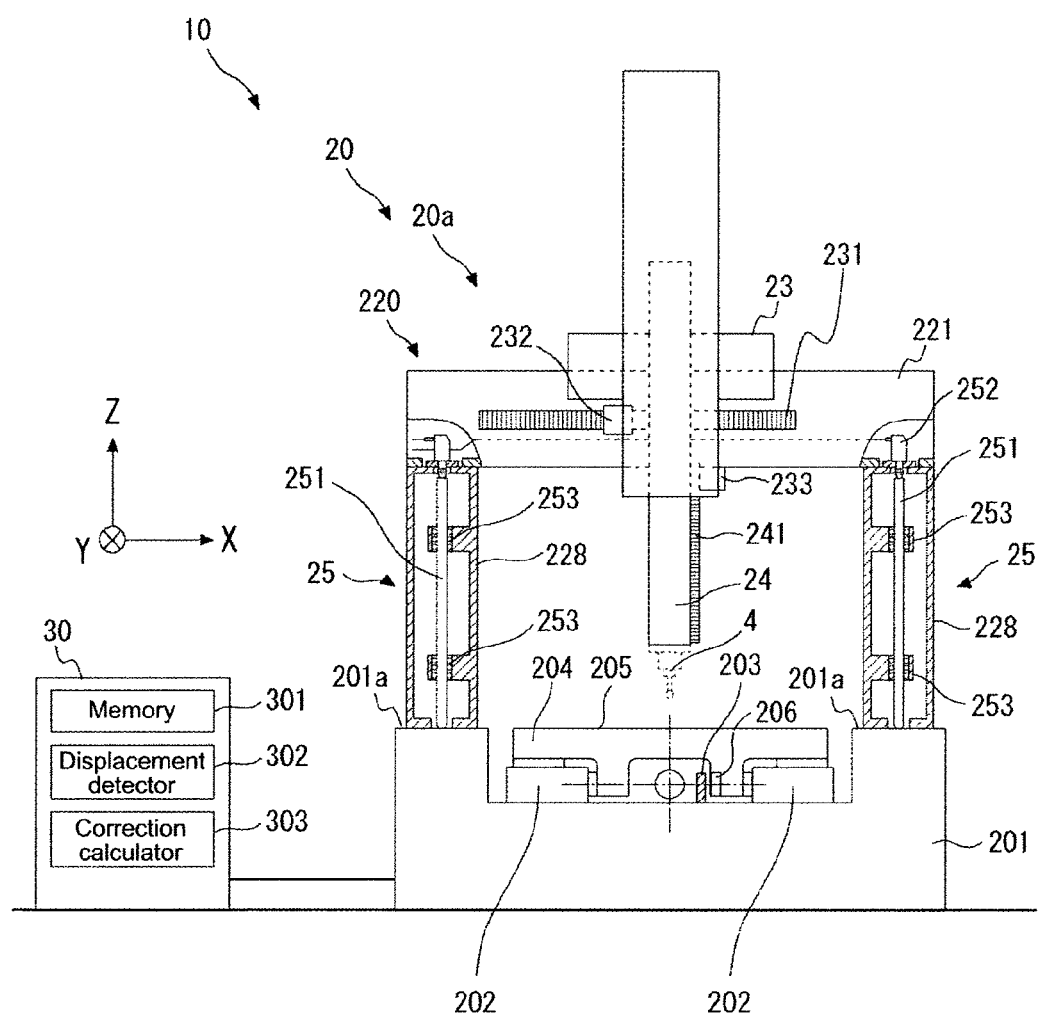
FIG. 4 illustrates a schematic configuration of a coordinate measuring machine (industrial machine) according to a second embodiment.

FIG. 4 illustrates a schematic configuration of the coordinate measuring machine (the industrial machine) according to the second embodiment. In FIG. 4, a coordinate measuring machine 10 includes a measurer main body 20; a controller 30 executing drive control of the measurer main body 20, a process calculating three-dimensional coordinate values, and the like; and a probe 4 outputting to the controller 30 a signal indicating contact between a stylus head and a work piece W (measured object, not shown in FIG. 4) or a signal for an amount of displacement of the stylus head due to the contact. The coordinate measuring machine 10 is a fixed bridge-type coordinate measuring machine (a fixed bridge, table displacement-type coordinate measuring machine). In addition, in some cases, the coordinate measuring machine 10 is referred to as a bridge structure-type machine having triaxial orthogonal coordinates.

The measurer main body 20 includes a moving mechanism 20a moving the probe 4 relative to the work piece W using three displacement axes parallel to the X-axis direction, the Y-axis direction, and the Z-axis direction, respectively. The moving mechanism 20a includes, as primary structural components, a base 201, a fixed bridge 220, two Y-rails 202, a Y-table 204, the X-slider 23, and the Z-ram 24. The fixed bridge 220 is fixated to a top surface 201a of the base 201. The two Y-rails 202 are fixated to a recess formed in a center portion of the top surface 201a and extend in the Y-axis direction. The Y-table 204 is capable of movement over the base 201, guided by the two Y-rails 202. The X-slider 23 is supported by the fixed bridge 220 and is capable of movement relative to the fixed bridge 220 in the X-axis direction. The Z-ram 24 is supported by the X-slider 23 and is capable of movement relative to the X-slider 23 in the Z-axis direction. The Z-ram 24 also holds the probe 4.

The work piece W and the master ball 213 (not shown in FIG. 4) are placed on a top surface 205 of the Y-table 204. The top surface 205 is orthogonal to the Z-axis direction. A Z-axis direction position of the top surface 205 of the Y-table 204 substantially matches the Z-axis direction position of the top surface 201a of the base 201. The Y-table 204 is supported by the base 201 via the two Y-rails 202, and moves in the Y-axis direction relative to the base 201 so as to pass below the fixed bridge 220. The fixed bridge 220 includes two columns 228, each standing upright along the Z-axis direction on two sides in the X-axis direction straddling the Y-table 204, and the X-beam 221, which extends in the X-axis direction. The two columns 228 are fixated to the top surface 201a of the base 201, separated from each other in the X-axis direction. The X-beam 221 is supported by the two columns 228 and guides the X-slider 23 in the X-axis direction.

A hollow space is formed on an interior of the two columns 228. The Z correction reference unit 25 is provided to each of the columns 228. The Z correction reference unit 25 includes the low thermal expansion shaft 251, which is provided in the hollow space of the column 228; the guide unit 253 supporting the low thermal expansion shaft 251 within the hollow space of the column 228 so as to be parallel to the Z-axis direction; and the displacement sensor 252 detecting a relative Z-axis direction displacement of the column 228, using the low thermal expansion shaft 251 as a reference. The thermal expansion coefficient of the material forming the low thermal expansion shaft 251 is smaller than the thermal expansion coefficient of the material forming the columns 228.

The bottom end of the low thermal expansion shaft 251 is in contact with the top surface 201a of the base 201. Accordingly, the bottom end of the low thermal expansion shaft 251 is a fixed end fixated so as to prevent displacement in the Z-axis direction relative to a bottom end (base 201-side end) of the column 228. Moreover, the bottom end of the low thermal expansion shaft 251 is not necessarily supported by the top surface 201a, and may instead be supported by the bottom end of the column 228, proximate to the top surface 201a.

The guide unit 253 supports the low thermal expansion shaft 251 without restricting relative Z-axis direction displacement due to a difference in the amount of expansion/ contraction between the low thermal expansion shaft 251 and the column 228. Accordingly, a top end of the low thermal expansion shaft 251 is a free end allowing unrestricted displacement in the Z-axis direction relative to a top end of the column 228 due to a difference in thermal expansion between the low thermal expansion shaft 251 and the column 228. The displacement sensor 252 is provided to the top end (e.g., the top surface) of the column 228 and directly measures, using the top end of the low thermal expansion shaft 251 as the reference, the amount of Z-axis direction expansion/contraction of the column 228, the expansion/contraction occurring due to a change in temperature, then outputs a measurement signal to the controller 30.

Accordingly, the amount of expansion/contraction due to a change in temperature can be accurately measured for the column 228, which is a structural element of the moving mechanism 20*a* of the coordinate measuring machine 10.

The measurer main body 20 includes the X-scale 231 and the X-detection device 232 for measuring an amount of X-axis direction displacement of the probe 4; a Y-scale 203 and a Y-detection device 206 for measuring an amount of Y-axis direction displacement of the probe 4; and the Z-scale 241 and the Z-detection device 233 for measuring an amount of Z-axis direction displacement of the probe 4. The X-detection device 232 reads a value of the X-scale 231, then outputs to the controller 30 a signal indicating the read result. The Y-scale 203 is fixated to the base 201 and extends in the Y-axis direction. The Y-detection device 206 is provided to the Y-table 204 and reads a value of the Y-scale 203, then outputs to the controller 30 a signal indicating the read result. The Z-detection device 233 is provided to the X-slider 23 and reads a value of the Z-scale 241, then outputs to the controller 30 a signal indicating the read result.

The controller 30 includes a memory 301, a displacement detector 302, and a correction calculator 303. The controller 30, the memory 301, the displacement detector 302, and the correction calculator 303 correspond, respectively, to the controller 3, the memory 31, the displacement detector 32, and the correction calculator 33 according to the first embodiment. The displacement detector 302 calculates an amount of displacement based on the measurement signal output by the displacement sensor 252. For example, the displacement detector 302 calculates the amount of Z-axis direction displacement of the X-slider 23 or the Z-ram 24 caused by expansion and contraction of the two columns 228. The correction calculator 303 performs correction based on the amount of displacement calculated by the displacement detector 302. In other words, the controller 30 can calculate the coordinates of the probe 4 or the work piece W based on the amount of Z-axis direction expansion/contraction of the columns 228 due to a change in temperature.

Given the above, the Z-axis direction displacement due to a change in temperature can be corrected using the amount of Z-axis direction expansion/contraction of the columns 228, which is measured by the Z correction reference unit 25. Accordingly, the Z coordinate in the "machine coordinate system" of the coordinate measuring machine 10 can achieve a degree of thermal stability equivalent to a case where the columns 228 are formed with a low thermal expansion material.

Furthermore, the amounts of Z-axis direction expansion/contraction of the two columns 228 are measured individually. Therefore, sloping of the X-beam 221 in the XZ plane and slant of the Z axis in the XZ plane (rotation of the Z axis around the Y axis) can be detected. In addition, the Z-axis direction position of the bottom end of the low thermal expansion shaft 251 (the fixed end) substantially matches the Z-axis direction position of the top surface 205 of the Y-table 204, where the work piece W and the master ball 213 are placed. The Z-axis direction position of the top end of the low thermal expansion shaft 251 (the reference point for measuring the amount of expansion/contraction) substantially matches the Z-axis direction position of the detection reference point O of the Z-detection device 233. Therefore, the relative Z-axis direction displacement in the "machine coordinate system" and the "work piece coordinate system" due to a change in temperature can be more accurately detected.

Third Embodiment

Figure 5:
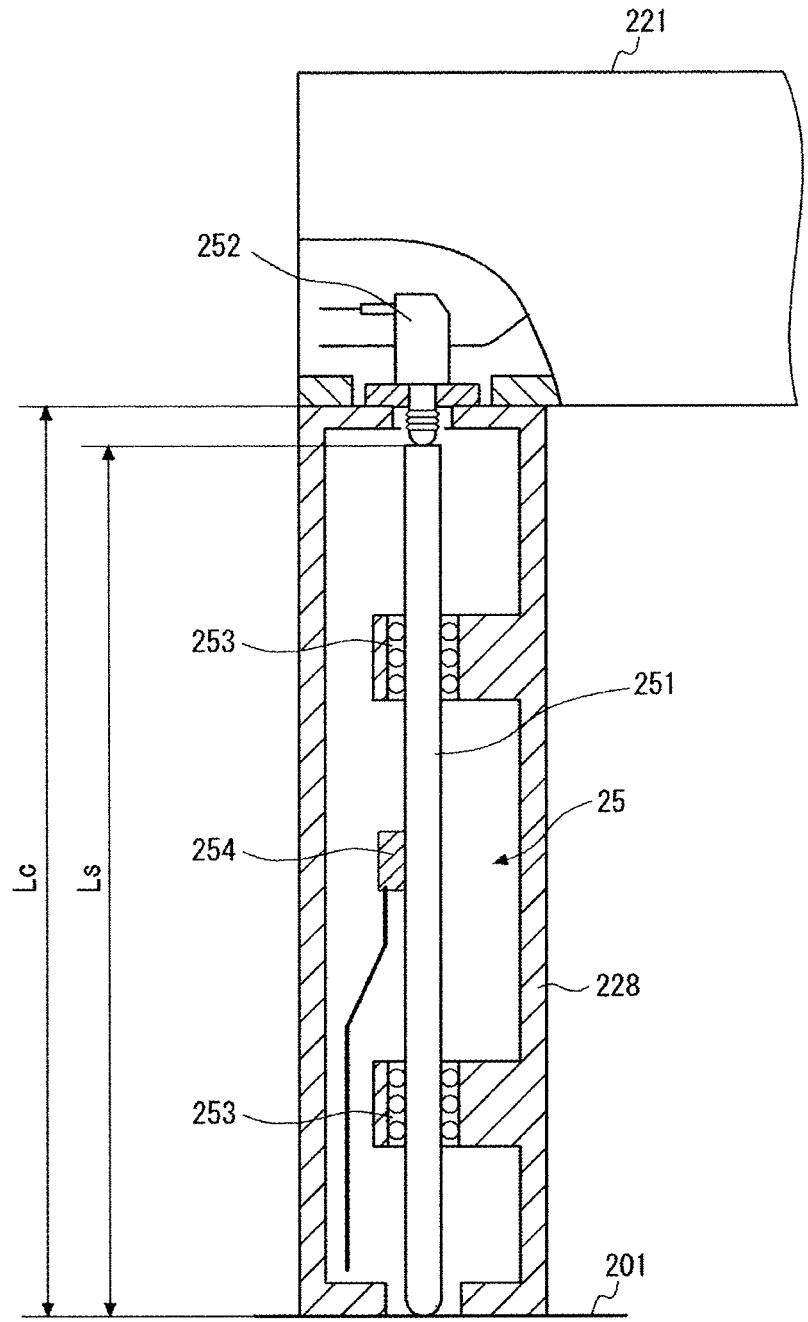
FIG. 5 illustrates a schematic configuration of a Z correction reference unit according to a third embodiment.

Next, a Z correction reference unit according to a third embodiment is described. Descriptions of aspects common to both the first and second embodiments may be omitted. FIG. 5 illustrates a schematic configuration of the Z correction reference unit according to the third embodiment. The Z correction reference unit 25 according to the third embodiment can be applied to either of the first and second embodiments. FIG. 5 illustrates an example in which the Z correction reference unit 25 according to the third embodiment is provided to the column 228; however, the Z correction reference unit 25 can also be provided to the column 222 or the supporter 223.

The Z correction reference unit 25 according to the third embodiment includes a temperature detection sensor 254 attached to the low thermal expansion shaft 251. The temperature detection sensor 254 detects a temperature of the low thermal expansion shaft 251 and outputs the detected temperature to one of the controller 3 and the controller 30. One of the controller 3 and the controller 30 calculates the amount of expansion/contraction of the low thermal expansion shaft 251 based on the temperature of the low thermal expansion shaft 251, the thermal expansion coefficient of the low thermal expansion shaft 251, and a length Ls of the low thermal expansion shaft 251 at a reference temperature (e.g., 20° C.). Moreover, one of the controller 3 and the controller 30 corrects the amount of expansion/contraction of one of the column 222, the supporter 223, and the column 228, which was measured by the displacement sensor 252, based on the amount of expansion/contraction of the low thermal expansion shaft 251. Thereby, the amount of expansion/contraction of one of the column 222, the supporter 223, and the column 228 can be more accurately measured. In addition, using a low thermal expansion material such as Invar or Super Invar as the material forming the adjustment screw 224 supporting the low thermal expansion shaft 251 is also effective.

Fourth Embodiment

Figure 6:
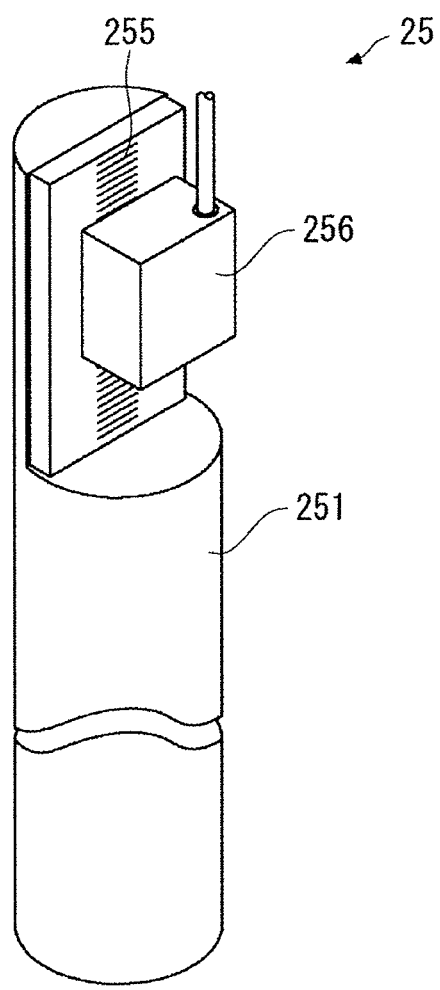
FIG. 6 is a perspective view of a schematic configuration of a Z correction reference unit according to a fourth embodiment.

Next, a Z correction reference unit according to a fourth embodiment is described. Descriptions of aspects common to the first through third embodiments may be omitted. FIG. 6 illustrates a schematic configuration of the Z correction reference unit according to the fourth embodiment. The Z correction reference unit 25 according to the fourth embodiment can be applied to any one of the first through third embodiments.

The Z correction reference unit 25 according to the fourth embodiment can include a linear scale 255 and a linear encoder 256 instead of the displacement sensor 252, which included the plunger-type contact stylus head 252*a*. The linear scale 255 is formed with a low thermal expansion material such as a low thermal expansion glass ceramic, and is fixated to the top end of the low thermal expansion shaft 251. The linear encoder 256 is an optical displacement sensor fixated to the top end of one of the column 222, the supporter 223, and the column 228, and measuring the amount of expansion/contraction of one of the column 222, the supporter 223, and the column 228 based on the linear scale 255.

Moreover, in order to measure the amount of expansion/contraction of one of the column 222, the supporter 223, and the column 228, a non-contact-type displacement sensor may also be used, such as an eddy current-type displacement sensor, a capacitance-type displacement sensor, and an optical displacement sensor using laser interference. In a case where the capacitance-type displacement sensor is used, a measurement surface of the capacitance-type displacement sensor is a top end surface of the low thermal expansion shaft 251.

Fifth Embodiment

Figure 7:
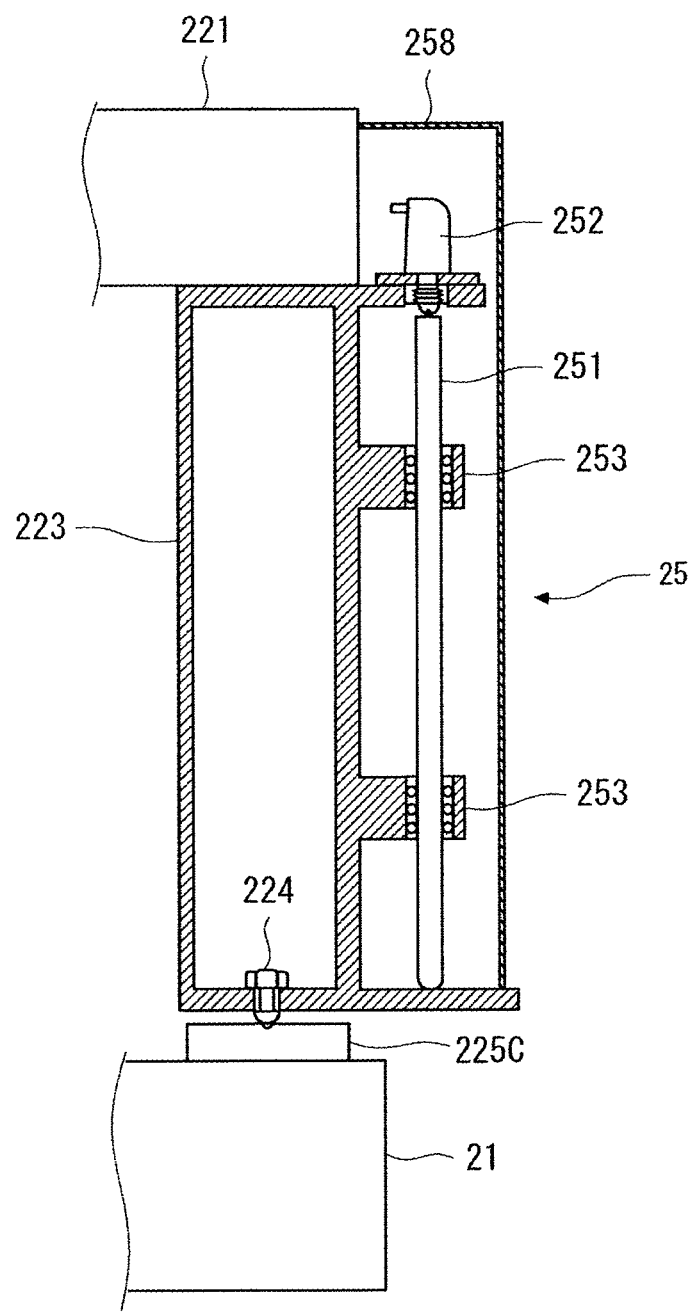
FIG. 7 illustrates a schematic configuration of a Z correction reference unit according to a fifth embodiment.

Next, a Z correction reference unit according to a fifth embodiment is described. Descriptions of aspects common to the first through fourth embodiments may be omitted. FIG. 7 illustrates a schematic configuration of the Z correction reference unit according to the fifth embodiment. The Z correction reference unit 25 according to the fifth embodiment can also be applied to any one of the first through fourth embodiments. FIG. 7 illustrates an example in which the Z correction reference unit 25 according to the fifth embodiment is provided to the supporter 223; however, the Z correction reference unit 25 can also be provided to the columns 222 or 228.

In the Z correction reference unit 25 according to the fifth embodiment, the low thermal expansion shaft 251 is positioned outside one of the column 222, the supporter 223, and the column 228. The fifth embodiment is effective in a case where the Z correction reference unit 25 is later attached to an existing coordinate measuring machine, or in a case where no hollow space is formed on the interior of the column 222, the supporter 223, and the column 228. Even in a case where the low thermal expansion shaft 251 is positioned outside one of the column 222, the supporter 223, and the column 228, by covering the low thermal expansion shaft 251 with a cover 258, the low thermal expansion shaft 251 can be made unlikely to be influenced by environmental changes in temperature. When the cover 258 is formed with an insulating material, the low thermal expansion shaft 251 can be made even more unlikely to be influenced by environmental changes in temperature.

(Observations Regarding Amount of Expansion/contraction of Low Thermal Expansion Shaft, Column, and Supporter)

Next, the amount of expansion/contraction of the low thermal expansion shaft 251, the column 222, the supporter 223, and the column 228 due to environmental changes in temperature is considered for a case where Super Invar is used as the material forming the low thermal expansion shaft 251 and an aluminum-based alloy material is used as the material forming the column 222, the supporter 223, and the column 228. A thermal expansion coefficient $\alpha_I$ of Super Invar, which forms the low thermal expansion shaft 251, is $0.5 \times 10^{-6}$/K, which is approximately 1/45 of the thermal expansion coefficient of the aluminum-based alloy material forming the column 222, the supporter 223, and the column 228.

For example, when a range of environmental temperature change $\Delta T$ is 9K (17° C. to 26° C.) and the length Ls of the low thermal expansion shaft 251 (approximately equal to the column height Lc) is approximately 1000 mm, an amount of expansion/contraction $\Delta Ls$ of the length Ls of the low thermal expansion shaft 251 is expressed by the following formula.

[Formula 1]

$$\Delta Ls = Ls \times \alpha_I \times \Delta T \quad (1)$$
$$= 1000[\text{mm}] \times 0.5 \times 10^{-6}[K^{-1}] \times 9[K]$$
$$= 0.0045[\text{mm}]$$
$$= 4.5[\mu\text{m}]$$

Accordingly, the Z-axis direction displacement of the low thermal expansion shaft 251, which is the reference for correction, is 4.5 μm.

Herein, in a case where a temperature correction is applied to the low thermal expansion shaft 251 as in the third embodiment, when an unreliability $\delta\alpha_I$ of the thermal expansion coefficient of the Super Invar material is defined at 20% of a nominal value and a detection unreliability $\delta T$ of the temperature detection sensor 254 is defined at 20% of a detection range, an unreliability $\delta Ls$ of an amount of temperature correction is expressed by the following formula.

[Formula 2]

$$\delta Ls = Ls \times \delta\alpha_I \times \delta T \quad (2)$$
$$= 1000[\text{mm}] \times 0.1 \times 10^{-6}[K^{-1}] \times 1.8[K]$$
$$= 0.00018[\text{mm}]$$
$$= 0.18[\mu\text{m}]$$

Accordingly, more highly accurate correction becomes possible, using the low thermal expansion shaft 251 as a more accurate length reference.

In this connection, the thermal expansion coefficient $\alpha_A$ of the aluminum-based alloy material forming the column 222, the supporter 223, and the column 228 is approximately $22.5 \times 10^{-6}$/K. For example, when the range of environmental temperature change $\Delta T$ is 9K (17° C. to 26° C.) and the column height Lc is approximately 1000 mm, the amount of expansion/contraction $\Delta Lc$ of the column height Lc is expressed by the following formula.

[Formula 3]

$$\Delta Lc = Lc \times \alpha_A \times \Delta T \quad (3)$$
$$= 1000[\text{mm}] \times 22.5 \times 10^{-6}[K^{-1}] \times 9[K]$$
$$= 0.2025[\text{mm}]$$
$$= 202.5[\mu\text{m}]$$

Figure 8A:
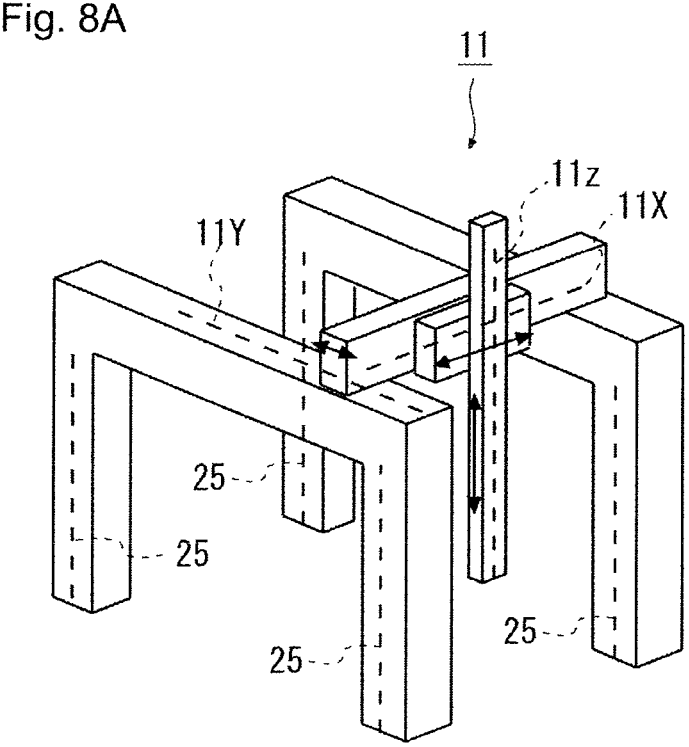
FIG. 8A illustrates a schematic configuration of a coordinate measuring machine (industrial machine) according to a first modification.

Moreover, the present invention is not limited to the embodiments described above, and may be modified as needed without departing from the scope of the present invention. For example, as shown in FIG. 8A, an industrial machine 11 according to a first modification is a bridge/floor-type (gantry-type) coordinate measuring machine. The industrial machine 11 includes an X-scale 11X, a Y-scale 11Y, a Z-scale 11Z, and the Z correction reference unit 25.

Figure 8B:
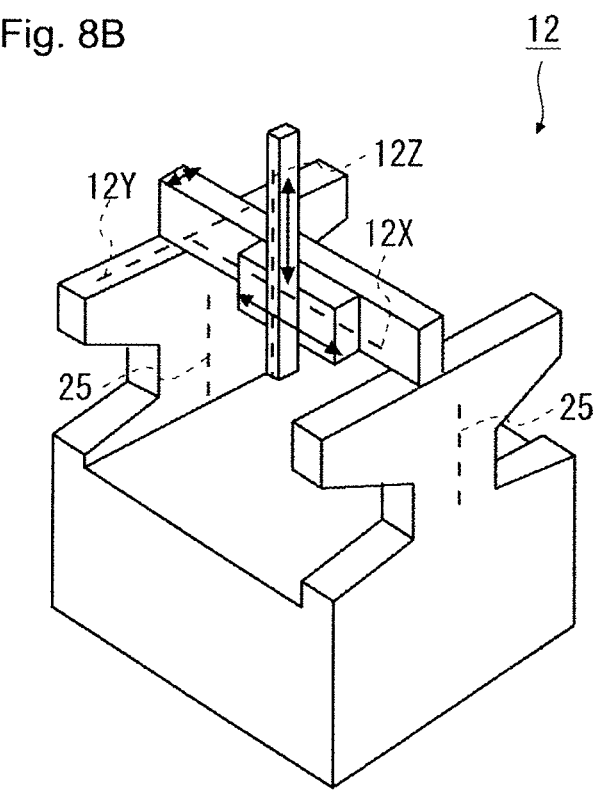
FIG. 8B illustrates a schematic configuration of a coordinate measuring machine (industrial machine) according to a second modification.

As shown in FIG. 8B, an industrial machine 12 according to a second modification is a bridge/bed-type coordinate measuring machine. The industrial machine 12 includes an X-scale 12X, a Y-scale 12Y, a Z-scale 12Z, and the Z correction reference unit 25.

Figure 8C:
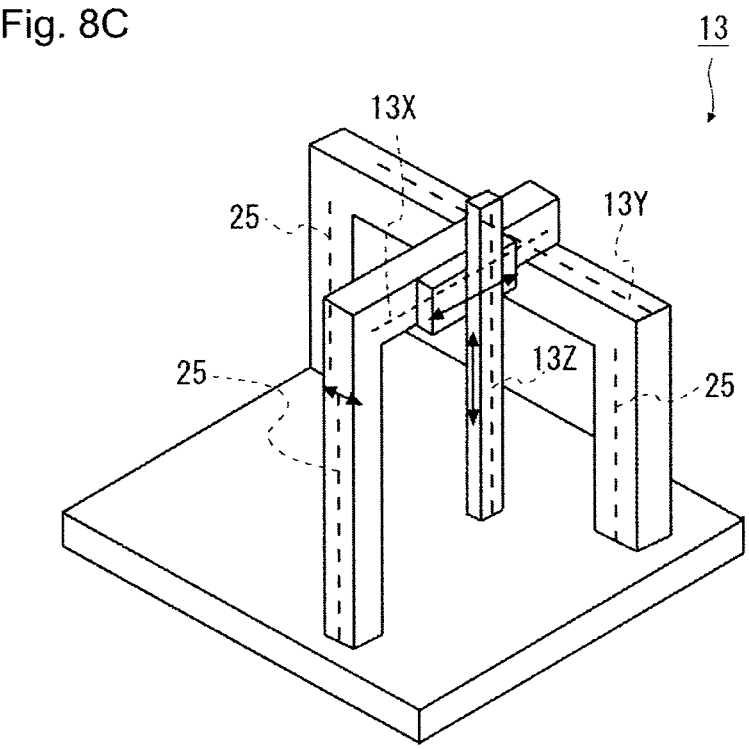
FIG. 8C illustrates a schematic configuration of a coordinate measuring machine (industrial machine) according to a third modification.
Figure 8D:
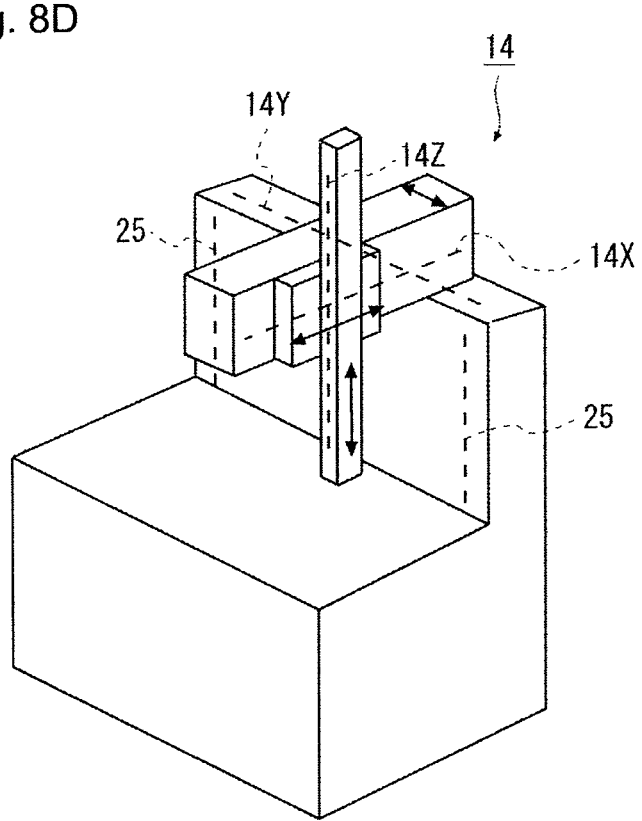
FIG. 8D illustrates a schematic configuration of a coordinate measuring machine (industrial machine) according to a fourth modification.

As shown in FIG. 8C, an industrial machine 13 according to a third modification is an L-shaped bridge-type coordinate measuring machine. The industrial machine 13 includes an X-scale 13X, a Y-scale 13Y, a Z-scale 13Z, and the Z correction reference unit 25. As shown in FIG. 8D, an industrial machine 14 according to a fourth modification is a cantilever Y-axis displacement-type coordinate measuring machine. The industrial machine 14 includes an X-scale 14X, a Y-scale 14Y, a Z-scale 14Z, and the Z correction reference unit 25.

Figure 8E:
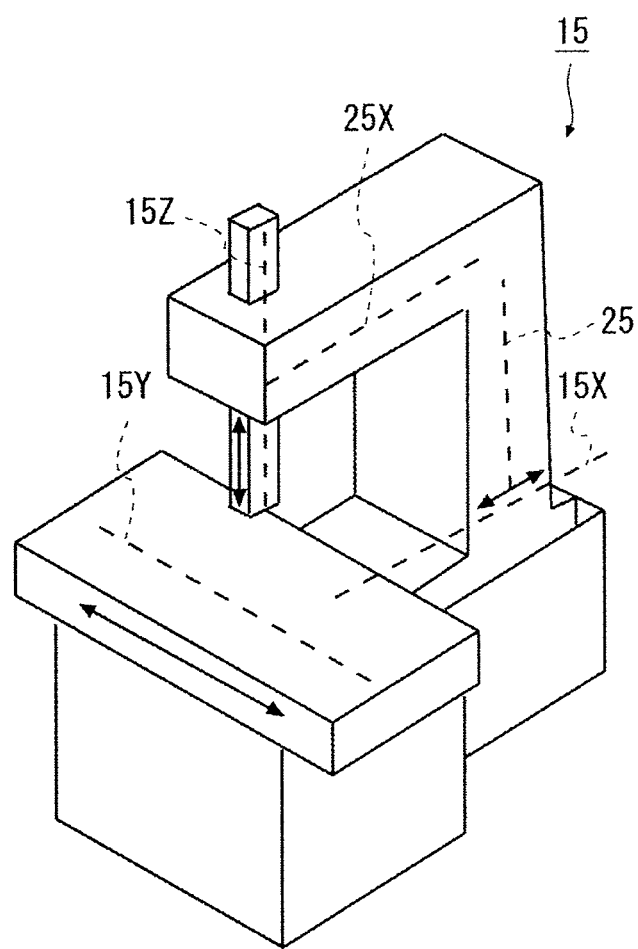
FIG. 8E illustrates a schematic configuration of a coordinate measuring machine (industrial machine) according to a fifth modification.
Figure 8F:
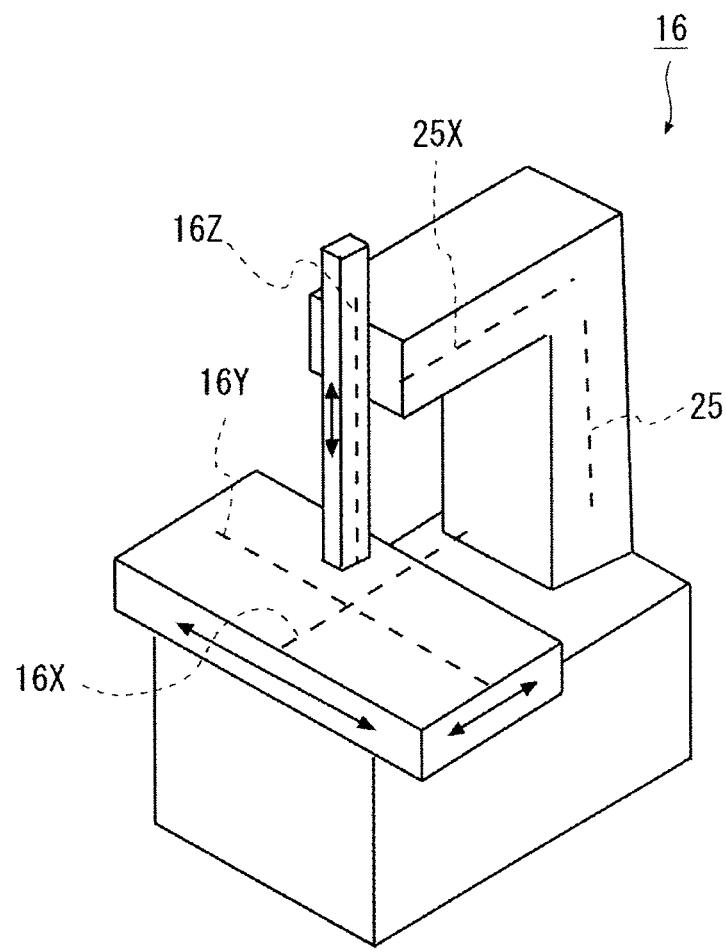
FIG. 8F illustrates a schematic configuration of a coordinate measuring machine (industrial machine) according to a sixth modification.

As shown in FIG. 8E, an industrial machine 15 according to a fifth modification is a single column column-displacement-type coordinate measuring machine. The industrial machine 15 includes an X-scale 15X, a Y-scale 15Y, a Z-scale 15Z, the Z correction reference unit 25, and an X correction reference unit 25X. As shown in FIG. 8F, an industrial machine 16 according to a sixth modification is a single column XY table-type coordinate measuring machine. The industrial machine 16 includes an X-scale 16X, a Y-scale 16Y, a Z-scale 16Z, the Z correction reference unit 25, and the X correction reference unit 25X.

Figure 8G:
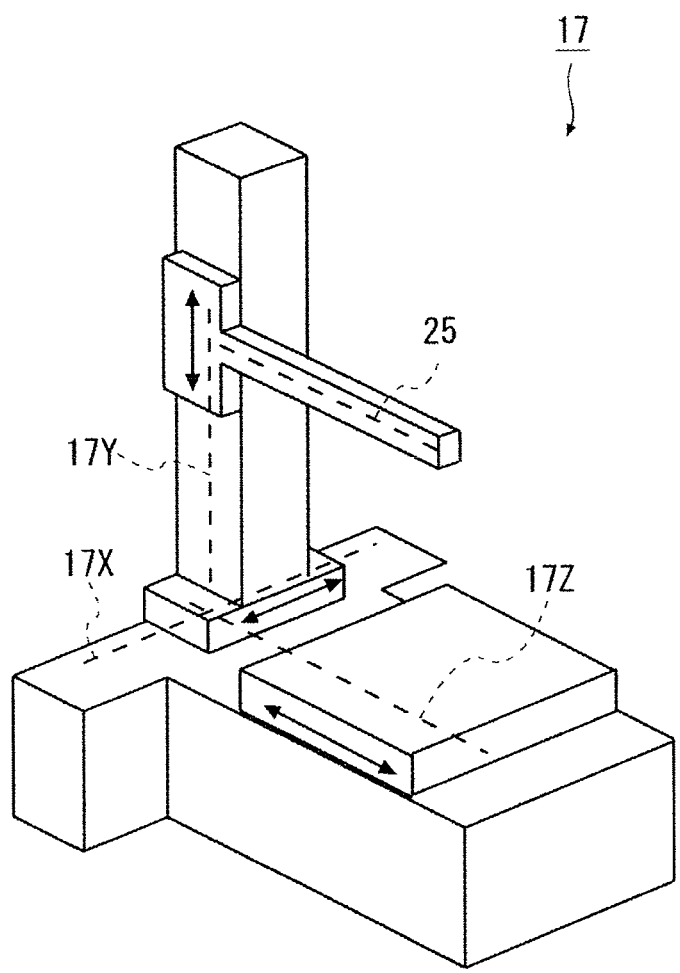
FIG. 8G illustrates a schematic configuration of a coordinate measuring machine (industrial machine) according to a seventh modification.
Figure 8H:
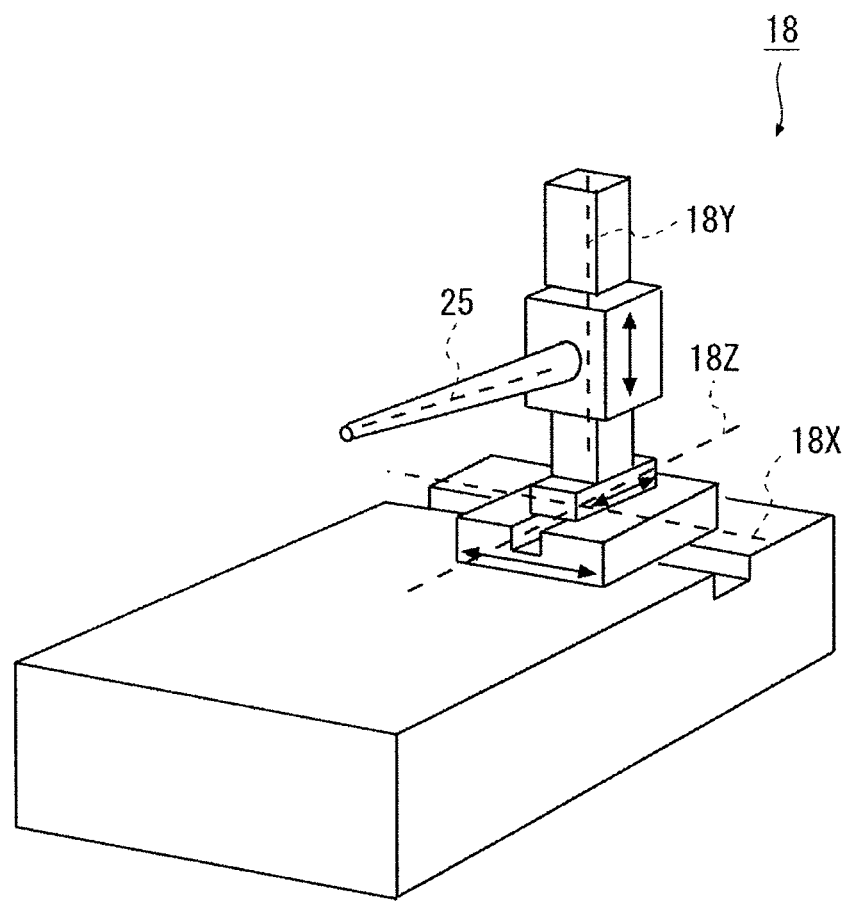
FIG. 8H illustrates a schematic configuration of a coordinate measuring machine (industrial machine) according to an eighth modification.

As shown in FIG. 8G, an industrial machine 17 according to a seventh modification is a horizontal arm table-displacement-type coordinate measuring machine. The industrial machine 17 includes an X-scale 17X, a Y-scale 17Y, a Z-scale 17Z, and the Z correction reference unit 25. As shown in FIG. 8H, an industrial machine 18 according to an eighth modification is a horizontal arm fixed table-type coordinate measuring machine. The industrial machine 18 includes an X-scale 18X, a Y-scale 18Y, a Z-scale 18Z, and the Z correction reference unit 25. The industrial machines 11 to 18 may also be machine tools.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. An industrial machine comprising:
    a moving mechanism configured to move one of a probe and a tool relative to a work piece, by using three moving axes parallel to each of three orthogonal axis directions;
    a low thermal expansion member comprising a material having a smaller thermal expansion coefficient than a material forming a structural element of the moving mechanism; and
    an expansion/contraction measurer configured to measure, using the low thermal expansion member as a reference, an amount of expansion/contraction of the structural element in one of the three orthogonal axis directions, the expansion/contraction occurring due to a change in temperature.

2. The industrial machine according to claim 1, wherein the low thermal expansion member is provided in a hollow space located on an interior of the structural element.

3. The industrial machine according to claim 1, wherein the expansion/contraction measurer includes one of a differential transformer-type displacement sensor having a contact stylus head, an eddy current-type displacement sensor, a capacitance-type displacement sensor, and an optical displacement sensor.

4. The industrial machine according to claim 1, further comprising:
    a temperature detection sensor configured to detect the temperature of the low thermal expansion member; and
    an expansion/contraction corrector configured to calculate the amount of expansion/contraction of the low thermal expansion member based on the temperature, the thermal expansion coefficient of the low thermal expansion member, and dimensions of the low thermal expansion member at a reference temperature, the expansion/contraction corrector further configured to correct the amount of expansion/contraction of the structural element based on the amount of expansion/contraction of the low thermal expansion member.

5. The industrial machine according to claim 1, wherein:
    the three orthogonal axis directions include an X-axis direction, a Y-axis direction, and a Z-axis direction,
    the moving mechanism comprises:
        a base;
        a Y-table supported by the base and configured to be moved in the Y-axis direction relative to the base;
        a fixed bridge affixed to the base;
        an X-slider supported by the fixed bridge and configured to be moved in the X-axis direction relative to the fixed bridge; and
        a Z-ram supported by the X-slider, and configured to be moved in the Z-axis direction relative to the X-slider, the Z-ram further configured to hold one of the probe and the tool,
    a top surface on which the work piece is configured to be installed is formed on the Y-table,
    the top surface of the Y-table is orthogonal to the Z-axis direction,
    the fixed bridge comprises:
        a first column and a second column, each standing upright along the Z-axis direction on two sides in the X-axis direction straddling the Y-table; and
        an X-beam supported by the first column and the second column and configured to guide the X-slider in the X-axis direction,
    the low thermal expansion member comprises:
        a first low thermal expansion member comprising a material having a smaller thermal expansion coefficient than the material forming the first column; and
        a second low thermal expansion member comprising a material having a smaller thermal expansion coefficient than the material forming the second column, and
    the expansion/contraction measurer is further configured to measure the amount of Z-axis direction expansion/contraction of the first column by using the first low thermal expansion member as the reference, and is further configured to measure the amount of Z-axis direction expansion/contraction of the second column by using the second low thermal expansion member as the reference.

6. The industrial machine according to claim 5 further comprising:
a Z-scale fixated to the Z-ram and extending in the Z-axis direction; and
a Z-detection device provided to the X-slider and configured to read a value of the Z-scale, wherein:
the first low thermal expansion member comprises a first top end and a first bottom end positioned respectively at each of two Z-axis direction sides,
the first bottom end is fixed so as to prevent displacement in the Z-axis direction relative to a base-side end of the first column, and the first top end is allowed to freely displace in the Z-axis direction relative to the first column due to a difference in thermal expansion between the first low thermal expansion member and the first column,
the second low thermal expansion member comprising a second top end and a second bottom end positioned respectively at each of two Z-axis direction sides,
the second bottom end is fixed so as to prevent displacement in the Z-axis direction relative to a base-side end of the second column, and the second top end is allowed to freely displace in the Z-axis direction relative to the second column due to a difference in thermal expansion between the second low thermal expansion member and the second column,
the expansion/contraction measurer is further configured to measure the amount of Z-axis direction expansion/contraction of the first column by using the first top end as a reference, and is further configured to measure the amount of Z-axis direction expansion/contraction of the second column by using the second top end as the reference,
Z-axis direction positions of the first bottom end and the second bottom end generally match a Z-axis direction position of the top surface of the Y-table, and
Z-axis direction positions of the first top end and the second top end generally match a Z-axis direction position of a detection reference point of the Z-detection device.

7. The industrial machine according to claim 1, wherein:
the three orthogonal axis directions include an X-axis direction, a Y-axis direction, and a Z-axis direction,
the moving mechanism comprises:
a base having a top surface configured to accept a work piece to be installed thereon;
a Y-carriage having a bridge structure supported by the base and configured to be moved in the Y-axis direction relative to the base;
an X-slider supported by the Y-carriage and configured to be moved in the X-axis direction relative to the Y-carriage; and
a Z-ram supported by the X-slider, configured to be moved in the Z-axis direction relative to the X-slider, and further configured to hold one of the probe and the tool,
the top surface of the base is orthogonal to the Z-axis direction,
the Y-carriage comprises:
a column and a supporter, each standing upright along the Z-axis direction, separated from each other in the X-axis direction; and
an X-beam supported by the column and the supporter and configured to guide the X-slider in the X-axis direction,
the low thermal expansion member comprises:
a first low thermal expansion member comprising a material having a smaller thermal expansion coefficient than the material forming the column; and
a second low thermal expansion member comprising a material having a smaller thermal expansion coefficient than the material forming the supporter, and
the expansion/contraction measurer is further configured to measure the amount of Z-axis direction expansion/contraction of the column by using the first low thermal expansion member as a reference, and is further configured to measure the amount of Z-axis direction expansion/contraction of the supporter by using the second low thermal expansion member as the reference.

8. The industrial machine according to claim 7, further comprising:
a Z-scale fixated to the Z-ram and extending in the Z-axis direction; and
a Z-detection device provided to the X-slider and reading a value of the Z-scale, wherein:
the first low thermal expansion member comprises a first top end and a first bottom end positioned respectively at each of two Z-axis direction sides,
the first bottom end is fixated so as to prevent displacement in the Z-axis direction relative to a base-side end of the column and the first top end is allowed to freely displace in the Z-axis direction relative to the column due to a difference in thermal expansion between the first low thermal expansion member and the column, and
the second low thermal expansion member comprises a second top end and a second bottom end positioned respectively at each of two Z-axis direction sides,
the second bottom end is fixated so as to prevent displacement in the Z-axis direction relative to a base-side end of the supporter and the second top end is allowed to freely displace in the Z-axis direction relative to the supporter due to a difference in thermal expansion between the second low thermal expansion member and the supporter,
the expansion/contraction measurer is further configured to measure the amount of Z-axis direction expansion/contraction of the column using the first top end as the reference, and is further configured to measure the amount of Z-axis direction expansion/contraction of the supporter by using the second top end as the reference,
Z-axis direction positions of the first bottom end and the second bottom end generally match a Z-axis direction position of the top surface of the base, and
Z-axis direction positions of the first top end and the second top end generally match a Z-axis direction position of a detection reference point of the Z-detection device.

9. The industrial machine according to claim 7, wherein:
the low thermal expansion member further comprises a third low thermal expansion member comprising a material having a smaller thermal expansion coefficient than the material forming the column,
the first low thermal expansion member is positioned at a first position of the column, the third low thermal expansion member is positioned at a second position of the column separated from the first position in the Y-axis direction, and the expansion/contraction measurer is further configured to measure the amount of Z-axis direction expansion/contraction of the column in the first position by using the first low thermal expansion member as the reference, and is further configured to measure the amount of Z-axis direction expansion/contraction of the column in the second position by using the third low thermal expansion member as the reference.

10. The industrial machine according to claim 9, further comprising:

a Z-scale fixated to the Z-ram and extending in the Z-axis direction; and a Z-detection device provided to the X-slider and reading a value of the Z-scale, wherein:

the first low thermal expansion member comprises a first top end and a first bottom end positioned respectively at each of two Z-axis direction sides, the first bottom end is fixated so as to prevent displacement in the Z-axis direction relative to a base-side end of the column and the first top end is allowed to freely displace in the Z-axis direction relative to the column due to a difference in thermal expansion between the first low thermal expansion member and the column, and the second low thermal expansion member comprises a second top end and a second bottom end positioned respectively at each of two Z-axis direction sides, the second bottom end is fixated so as to prevent displacement in the Z-axis direction relative to a base-side end of the supporter and the second top end is allowed to freely displace in the Z-axis direction relative to the supporter due to a difference in thermal expansion between the second low thermal expansion member and the supporter, the expansion/contraction measurer is further configured to measure the amount of Z-axis direction expansion/contraction of the column using the first top end as the reference, and is further configured to measure the amount of Z-axis direction expansion/contraction of the supporter by using the second top end as the reference, Z-axis direction positions of the first bottom end and the second bottom end generally match a Z-axis direction position of the top surface of the base, and Z-axis direction positions of the first top end and the second top end generally match a Z-axis direction position of a detection reference point of the Z-detection device.

11. A method for measuring an amount of expansion/contraction of an industrial machine having a moving mechanism moving one of a probe and a tool relative to a work piece, by using three moving axes parallel to each of three orthogonal axis directions, the method comprising measuring, using a low thermal expansion member as a reference, an amount of expansion/contraction of a structural element of the moving mechanism in one of the three orthogonal axis directions, the expansion/contraction occurring due to a change in temperature and the low thermal expansion member being formed with a material having a smaller thermal expansion coefficient than a material forming the structural element of the moving mechanism.

* * * * *